(12) United States Patent
Turner

(10) Patent No.: US 9,080,250 B2
(45) Date of Patent: Jul. 14, 2015

(54) METAL TREATMENT TO FORM A SURFACE LAYER

(75) Inventor: Andrew Derek Turner, Abingdon (GB)

(73) Assignee: Accentus Medical Limited, Didcot (GB)

( * ) Notice: Subject to any disclaimer, the term of this patent is extended or adjusted under 35 U.S.C. 154(b) by 599 days.

(21) Appl. No.: 13/262,344

(22) PCT Filed: Mar. 30, 2010

(86) PCT No.: PCT/GB2010/050535
§ 371 (c)(1),
(2), (4) Date: Sep. 30, 2011

(87) PCT Pub. No.: WO2010/112910
PCT Pub. Date: Oct. 7, 2010

(65) Prior Publication Data
US 2012/0024710 A1 Feb. 2, 2012

(30) Foreign Application Priority Data

Mar. 30, 2009 (GB) .................................. 0905354.7

(51) Int. Cl.
| | |
|---|---|
| *C25D 11/26* | (2006.01) |
| *A61L 27/04* | (2006.01) |
| *A61L 27/32* | (2006.01) |
| *A61L 27/54* | (2006.01) |
| *A61F 2/28* | (2006.01) |

(52) U.S. Cl.
CPC ................ *C25D 11/26* (2013.01); *A61L 27/04* (2013.01); *A61L 27/32* (2013.01); *A61L 27/54* (2013.01); *A61F 2/28* (2013.01); *A61L 2300/104* (2013.01); *A61L 2300/404* (2013.01); *A61L 2300/606* (2013.01); *A61L 2420/02* (2013.01)

(58) Field of Classification Search
CPC .. A61F 2/28–2/2875; A61F 2/30767–2/30771
USPC ........................................................ 205/229
See application file for complete search history.

(56) References Cited

U.S. PATENT DOCUMENTS

| | | | | |
|---|---|---|---|---|
| 5,340,605 A | * | 8/1994 | Silver et al. ................. | 427/126.3 |
| 2007/0181221 A1 | * | 8/2007 | Pickford et al. .............. | 148/239 |

FOREIGN PATENT DOCUMENTS

| | | | |
|---|---|---|---|
| WO | WO 2005/087982 A1 | | 9/2005 |
| WO | WO 2009/044203 A1 | | 4/2009 |

OTHER PUBLICATIONS

PCT Interrnational Search Report and Written Opinion for International Application No. PCT/GB2010/050535 dated Jun. 10, 2010.

* cited by examiner

*Primary Examiner* — James Lin
*Assistant Examiner* — Ho-Sung Chung
(74) *Attorney, Agent, or Firm* — Christensen O'Connor Johnson Kindness PLLC

(57) ABSTRACT

A metal object is treated to form an integral surface layer by: (a) immersing the metal object in an anodising electrolyte, and passivating the metal to form an anodised layer on the metal object; (b) continuing the application of a potential to modify the surface layer; (c) then treating the metal object with a chemical reducing agent so a hydrous metal oxide is formed; and (d) then contacting the metal object with a solution containing a biocidal material so as to incorporate biocidal material into the surface layer.

10 Claims, 1 Drawing Sheet

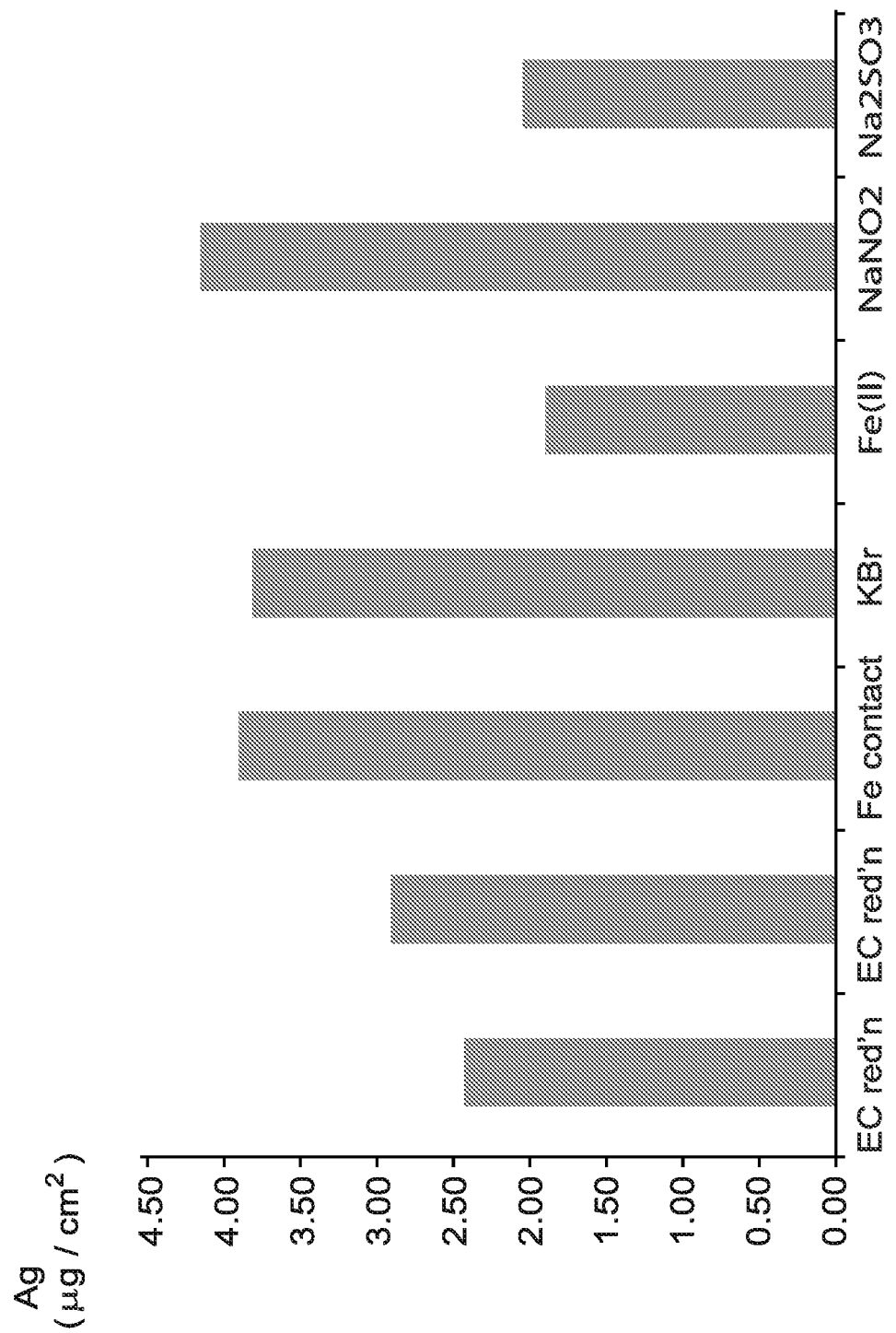

METAL TREATMENT TO FORM A SURFACE LAYER

The present invention relates to a method of treatment of a metal object to provide it with biocidal properties, together with a metal object produced by the method. In particular but not exclusively, the invention relates to treated metal objects that can be used to reduce irritation or infection in the body, for example with metal implants.

Metal objects come into contact with the body in numerous situations, for example in surgery, where implants are used, these implants being inserted into the tissue of the body, be this soft or hard tissue. In the case of cancer treatment of the bone for example, cancerous bone tissue is removed, and a prosthetic metal implant is used to replace that part of the bone that has been removed. Implants are also used for partial or full replacement of bones in joints (e.g. hips) and also in other fields such as dentistry and maxillofacial surgery. Implants for the foregoing (and other) uses may be of titanium metal or titanium alloy. Titanium metal and titanium alloy are biocompatible, relatively strong and relatively light.

Further, metal objects come into contact with the body in the case of jewellery. However, metal alloys may react with moisture in perspiration. Irritation and infection can occur not only for jewellery that pierces the body but also for jewellery that sits next to the skin if the wearer has sensitive skin.

As can be seen, in both the medical and jewellery fields, the use of metal which comes into contact with body tissue runs the risk of introducing infection, or infection occurring. In both areas it has been suggested that metallic silver might be electroplated onto metal. Silver is known to have biocidal properties and the silver controls infection without causing toxic effects to the subject. However such coatings may be undercut due to corrosion from body fluids and/or passivation of the implant surface, so that the coating may detach from the metal, which may lead to increased wear and cause tissue damage from detached particles containing silver.

The present invention seeks to overcome the problems associated with the prior art by providing an anodised metal object having both hardwearing and biocidal properties, which can reduce the risk of infection.

It is known to treat metal implants using electrochemical anodisation while applying a voltage to the metal which is in an electrolyte. During this process pits are produced in the surface of the metal. It is surmised that peroxy-titanyl cations are produced in surface pits during the anodisation of for example, a titanium or titanium alloy based material and these cations are held within the pit in the surface, unless the surface is subjected to stirring or rinsing. Peroxy-titanyl cations can be converted into hydrous titania $Ti(OH)_4$ within the pit by applying a reducing voltage (negative polarity or cathodic, compared with the positive voltage used for anodisation) but it has now been found that unexpectedly reduction can be carried out using chemical reductants.

According to a first aspect of the invention, there is provided a method of treating a metal object so as to form thereon a surface layer which is integral with the metal object, and which includes a biocidal material, the method comprising:
(a) immersing the metal object, which is to provide a substrate for the surface layer, in an anodising electrolyte containing a solvent, and passivating the metal to form an anodised integral surface layer on the metal object;
(b) continuing the application of a potential to produce pits through the integral surface and into the substrate;
(c) producing a hydrous metal oxide by treating the metal object with a chemical reducing agent after steps (a) and (b); and
(d) contacting the anodised metal object resulting from step (c) with a solution containing a biocidal material so as to incorporate said biocidal material into the surface layer.

In a preferred embodiment the chemical reducing agent is selected from one or more of the following—$KBr$, $NaI$, $Ti^{3+}$, $H_3PO_3$, $Fe^{2+}$, $NaNO_2$, $Na_2SO_3$. Alternatively, it is possible to connect a corrodible metal which is in solid form such as Fe or Zn, which preferably is immersed in the electrolyte, to the anodised work-piece to act as an external reductant, instead of using a liquid reagent; in this case the corrodible metal would be in contact with the metal object through an electrical connection, and would be in ionic connection with it through an electrolyte. The corrodible metal electrode corrodes preferentially, so causing electrochemical reduction at the surface of the metal object without the use of any external cell or source of electricity. The chemical reducing agent may be selected from one or more of the following: sodium sulphite, ferrous salts (chloride or sulphate), sodium nitrite, stannous chlorides or sulphates, chromous chlorides or sulphates, vanadous sulphates, hydrazine, borohydrides, or even acetone or formaldehyde under suitable conditions.

The chemical reducing agent concentration may be in the range 0.001 Molar to 5 Molar, more typically 0.1 to 1 Molar, a particularly useful concentration being 0.1 Molar. The invention is not limited to the chemical reducing agents disclosed. Preferably the chemical reducing agent is an acidic, electron donor which can reduce peroxy-cationic complexes whilst avoiding the production of unwanted by-products such as bromine. Preferably the chemical reducing agent does not contain complexants for Ti(IV) that might solubilise the hydrous titania, such as fluoride and oxalate anions.

In a preferred embodiment, the metal object is removed from the electrolyte solution after step (b) but it is not necessary to remove the object where the chemical reductant is based on a corrodible metal for example metallic iron or zinc, which for example may be immersed in an electrolyte.

It is envisaged that the electrolyte solution retained in the surface pits contains a peroxy-cationic complex, such as a peroxy-titanyl. On removal of the metal object from the anodising electrolyte, materials such as peroxy-titanyl will be carried in the pits in the surface of the metal object into the reducing solution where it will be reduced to hydrous titania.

The use of a chemical reducing agent solution results in hydrous metal oxides being produced and these oxides have a high surface area. The high surface area allows for increased ion exchange with materials such as silver, which can be used as biocidal materials.

In step (b) the metal object is anodised until pits are formed through said surface layer into the substrate metal and in step (d) the biocidal material is preferentially incorporated in said pits. The anodising is a two stage process with step (a) comprising the initial process of passivation i.e. preparing the surface for pitting by growing a surface film and then (b) pitting itself. The exact nature of these pits is not of concern; but in any event step (b) modifies the surface and thereby enhances its ability to absorb biocidal material in step (d).

The maximum voltage applied during anodisation can determine the thickness of the passive oxide film. Lower voltages applied subsequently may not affect the film thickness.

The voltage during passivation may be applied as a voltage increasing linearly with time to a limiting value or alternatively stepped voltages up to the maximum limit, or down to a lower subsequent value may be applied. It is also envisaged that multiple passivations may be used, where a voltage is applied repeatedly to prepare the metal surface for pitting.

These different types of applying voltage all come within the definition of applying a voltage.

Before moving on to step (d) there is preferably a step of rinsing of the anodised metal to remove residual electrolyte and/or chemical reducing agent, and then there is a subsequent contact with the solution containing the biocidal metals ions to incorporate the biocidal metal ions into the surface layer on the metal object. The rinsing may be by using water more preferably demineralised or deionised water or any appropriate solvent.

During the anodising procedure of steps (a) and (b), a positive voltage is applied to the metal. During step (c), the anodised and pitted metal material is immersed in a solution of the reductant in the form of a chemical reductant which has the effect of reducing peroxy-titanyl to hydrous titania. The chemical reduction occurs after the end of step (b) that was used to create the pits. By pits, we mean wells or reservoirs that are able to store the biocidal material. As a result of the anodising and subsequent steps, the metal object has a hard outer surface formed of an anodised layer, grown out from the surface (which can typically adsorb ~0.3-1.0 µg/cm$^2$ Ag), and dispersed over this layer are pits that can receive additional ions of the biocidal material such as silver ions. The matrix contained within the pits receiving the biocidal material may be relatively soft and porous compared to the hard anodised surface, thus combining the optimal properties of higher silver storage capacity with the harder anodised surface.

The biocidal material may comprise a biocidal metal and in particular, the biocidal metal is silver. It is envisaged that a colloidal type biocidal material may be used instead, for example a protein colloid adsorbed on the hydrous titania surface that could also release nutrients into a site in the body, which may assist in healing of the body where the implant is positioned.

The positive voltage in anodizing step (a) may be 1-200 V (volts) but typically is in the range of 30 V to 150 V, or even up to 750 V or 2000 V in an electrolyte with an appropriately high breakdown potential, such as lithium borate. Voltages that have been considered as useful are for example, 20V, 35V or 100V and these are particularly useful in the field of implants. After the growth of the passive layer (step (a)) of desired thickness, hardness and colour, pits may be grown in the surface in the same or different electrolyte, possibly at a lower potential, followed by the chemical reduction step to form hydrous titania in-situ.

Preferably, the biocidal material (e.g. metal, such as silver) is provided in the solution in the form of ions. The biocidal metal may be or may comprise silver, although other metals may be used in addition to or as alternatives to silver. The metal objects—such as treated implants—are effective for controlling or suppressing infection.

The anodising may be performed employing a liquid electrolyte preferably comprising phosphoric acid that has been dissolved in a solvent to make a more dilute solution to control the solution pH to within the desired range. The electrolyte may comprise water as solvent. Other electrolytes such as sulphuric acid, phosphate salt solutions or acetic acid may be used. Alkaline electrolytes such as sodium hydroxide may be used also. It is preferred that these electrolytes are in a diluted form for example 2.1M $H_3PO_4$, 0.1M $H_2SO_4$.

Preferably, movement or circulation of the electrolyte during anodising relative to the surface of the metal object during the anodising step is suppressed or inhibited, at least during the period when microscopic pits are being formed through the said surface layer (b), although during the passivation phase (a) when high currents flow gentle agitation is desirable to minimise the generation of local heating effects. This is beneficial in improving process uniformity over both a single item, but also between an assembly of units being treated simultaneously. For example, during the pit growth period (b), no stirring of the electrolyte should be performed, and/or means such as baffles or additives (such as gelling agents, to increase the viscosity of the electrolyte) to prevent or reduce electrolyte movement may be employed. It has been found that increased levels of hydrous metal oxide (e.g. hydrous titanium oxide) are formed in the pits when the electrolyte is not moved or circulated relative to the surface of the metal object during the part of the anodising step (b) when microscopic pits are being formed through the anodised surface layer into the substrate metal. It has also been found that higher levels of biocidal metal can be incorporated into sites on the thus anodised surface without giving rise to toxic effects when the resulting metal object is used.

The phosphoric acid may have a concentration in a range of from 0.01 M to 5.0 M, typically from 0.1 M to 3.0 M and in particular 2.0 M. An example of the concentration used in the medical field is 0.05 to 5.0 M, e.g. from 1.0 to 3.0 M and in the jewellery industry from 0.01 M to 5.0 M. Preferably, the pH of the acidic electrolyte should be maintained within the range of 0.5<pH<2.0—more ideally within the range 0.75<pH<1.75.

If an alkaline electrolyte is used the pH is preferably greater than 9 and more typically the pH is in the range of 10-14. The alkaline electrolyte can be a phosphate salt such as $Na_3PO_4$.

In instances where other anodising electrolytes are used instead of phosphoric acid, sulphuric acid or acetic acid may need to be adjusted to provide the desired effects due to factors such as changes in pH, or even temperature.

The geometric surface area of the metal object can be determined by conventional means such as Computer Aided Design (CAD) or the use of standard measuring devices such as, callipers, micrometers and rulers combined with a geometric model of the item being treated, or more advanced optical methods such as laser scanning. This measurement does not however take into account microscopic surface features or surface roughness of the metal. This microscopic surface area is an important factor in determining and controlling how much charge is passed during the anodisation step e.g. coulomb/cm$^2$. The microscopic surface area can be determined, for example, by immersion of the metal object (such as an orthopaedic implant) in an electrolyte, and measuring the double layer capacitance and comparing this to calibrated standards under identical conditions of temperature and electrolyte concentration. The charge or current per microscopic surface area e.g. coulomb/cm$^2$ or mA/cm$^2$ is therefore typically used in the control of the anodising process. The ratio of microscopic to geometric area is known as the surface roughness factor and can be used to convert one area to the other. For example, a 10 µg/cm$^2$ silver loading on a geometric area basis would correspond to a 5 µg/cm$^2$ silver loading on a microscopic areas basis for a roughness factor of 2.

The anodising may be performed with a maximum current density in a range of from 0.1 to 100 mA/cm$^2$, preferably 0.1 to 50 mA/cm$^2$, or more typically 1 to 10 mA/cm$^2$, e.g. 5 mA/cm$^2$ or thereabouts. This determines the time taken for passivation—i.e. the raising of the applied potential from 0 to the maximum value (e.g. of 100 V), when the current falls to a significantly lower value. Alternatively, an applied voltage linearly increasing with time or as voltage steps may be applied to control the passivation period; this in turn will have an influence on the subsequent pit growth phase (b). As an overview, typically, the initial value of the current density used in the pit-growth part of the process is typically in the range of 0.05-0.5 mA/cm² and the value for the current density at the end of this phase is typically in the range 0.2-5.0 mA/cm²

The amount of charge employed for anodising (steps (a) and (b)) may be in a range of from 1 to 10 coulombs/cm², e.g. from 2 to 5 coulomb/cm². The anodising current may be passed during a period of from 0.5 to 8 hours, more particularly 1 to 6 hours, e.g. from 2 to 4 hours.

The present invention also provides methods of treating a metal object as specified in one or more of the claims following this description.

According to a further aspect of the invention, there is provided a metal object obtained by the methods described above and hereinafter.

The metal object may be in the form of an implant, a medical implement or device or jewellery. In particular, in the case of a medical implement or device, this could include any type of device or tool that comes into contact with the body, for example pace-makers, stents, skin staples, scalpels, trocars, pins for bones or even medical implements such as scalpels or tissue clamps which are used during surgery.

The metal object has desirable biocidal properties to suppress and/or control infection without toxic effects on an individual, whether animal or human, that comes into contact with the material.

Implants according to the invention can be used for many medical and surgical purposes, including full and partial hip replacements, implants useful in maxillofacial, trauma, orthodontal and orthopaedic applications, dental implants, neurological apparatus and parts (such as staples, nails and pins) used in cardiovascular and general surgery.

The jewellery that can be made from the metal object according to the invention can include all types of jewellery. The jewellery can be conventional jewellery such as rings, necklaces and bracelets or the jewellery can be of the type that is held within an aperture in the body, for example jewellery that is applied to the body transcutaneously, i.e. the jewellery pierces the body e.g. earrings, navel rings, rings to be inserted through other fleshy parts of the body such as the lips, cheeks etc.

The metals that may be used to make the implants or jewellery according to the invention may be titanium or a titanium alloy. One standard alloy for this purpose is titanium 90% with 6% aluminium and 4% vanadium (British Standard 7252). Alternatively the metal may comprise niobium, tantalum or zirconium, or alloys of these metals.

For an implant or for jewellery it may be desirable that the surface of the material is highly polished before production of the surface layer by anodising. In the case of implants, a highly polished surface reduces any tendency for local calcification when the implant comes into contact with the bone. A polished surface also permits smooth movement of muscle and tissue over the surface with minimal fretting or wear. Suitable polishing may be attained by known techniques, such as (e.g.) mechanical or chemical polishing and/or electropolishing.

The metal object can initially be polished to provide a very smooth surface. Titanium alloy can be electro-polished using acetic acid, or a mixture of nitric and hydrofluoric acids. Alternatively the material might be subjected to a combination of anodic passivation with mechanical polishing, which may be referred to as electrolinishing, this process removing the oxide that protects surface roughness, the surface at that point then being electrochemically re-passivated, so producing a mirror-smooth finish. Various electrolytes are suitable for this purpose, including nitric acid mixed with sulphuric acid, sodium hydroxide, sodium phosphate, acetic acid or sodium hydroxide mixed with sodium nitrate. Techniques such as grit blasting or shot blasting or shot peening may also be used to prepare the surface (e.g. for subsequent application of hydroxyapatite by plasma spraying after biocidal ion loading, to stimulate localised bone attachment). Also, the surface may be spray coated with titanium to provide a rough surface.

After polishing or other treatment of the surface of the metal object, surface modification or conversion can take place, as described above. A hydrated metal oxide material (which may include some phosphate) is formed by anodising, followed by chemical reduction. Biocidal metal species are then absorbed into the oxide and/or phosphate matrix. The biocidal metal species may be in the form of ions, for example silver ions (or $Cu^{++}$), and these ions can be absorbed by ion exchange into the oxide and/or phosphate matrix. Cations of palladium, platinum or even ruthenium could be absorbed in a similar way. If desired, deposited silver, platinum or palladium ions could then be converted to metal, or deposited ruthenium ions converted to insoluble $RuO_2$, within the oxide or phosphate surface coating, this reaction being performed chemically or electrochemically or by light.

The invention is further described with reference to the accompanying figures and with reference to an embodiment of the invention which is given by way of a non-limitative example only.

FIG. 1: shows a graph of the silver loading as a function of reduction technique.

The implant may be first cleaned. The cleaning process may be by ultrasonic cleaning using first acetone as the liquid phase (or other degreasing solvent), then rinsed with fresh acetone (or other solvent) and followed by de-ionized water or any other suitable rinsing solution. The metal material may then be cleaned in a 1 M aqueous solution of sodium hydroxide (or other alkaline cleaner) and then rinsed in de-ionized water. The resulting cleaned metal material is then anodised in contact with an aqueous solution of phosphoric acid. The concentration of the phosphoric acid is preferably in a range of from 0.1-5 M, more typically from 1 to 3 M, e.g. 2 M (or about 20 weight percent of solution). The implant is anodised using a voltage in the range from 15 to 150 V, more typically 50 to 150 V e.g. 100 V. Such ranges may also apply to jewellery.

The voltage is preferably maintained until a desired growth of pits or pitted regions through the anodised surface layer into the substrate is attained. Preferably, the current density through the surface during anodising is monitored. A suitable current density limit during the initial film growth period is typically about 5 mA/cm², the voltage rising to a maximum constant value to produce a well anodised surface on the implant. The potential may be applied in a single step to its maximum value or it may be applied in steps, for example from 30 V to 80 V to 100V. Alternatively, the potential may be increased linearly to its maximum value at a controlled rate of 0.1-10 V/s, preferably 0.2-5 V/s, ideally 0.5-2 V/s. The desired degree of anodising is usually obtained after a charge of from 2 to 5 coulombs/cm² of surface area of the implant has been passed. Preferably, the anodising process is carried out over a period of from 0.25 to 6 hours, e.g. from 2 to 4 hours. A suitable charge would be about 3.5 coulombs/cm².

The surface of the thus-anodised implant comprises a hard layer comprising a titanium oxide, and pits or pitted regions. The pits and/or pitted regions are believed to contain titanium oxide and might also contain a soluble titanium compound. The pits typically have depths of up to 2 to 3 μm penetrating through the passive layer of typically 0.14 μm (at 100V) into the substrate and have diameters of up to 5 μm. The pits may occupy some 5 to 20% of the surface area, though preferably below 10%. However, depending on the voltage applied and the length of time of treatment, there may be a range of depths and diameters for the pits, for example the depths may range from 1 to 5 μm, more typically 1 to 4 μm and the diameters may be anywhere between 0.1 to 20 more typically 1 to 10 μm, or 1 to 5 μm and these ranges can vary across the surface of the implant.

During anodisation a voltage is applied to an electrolytic solution in which the implant is placed. Passivation of the surface of the metal occurs, which results in a material that is integral with the titanium metal substrate. During the initial application of voltage the potential is normally controlled using a current limiter which could be in the range of 2.5-10 mA/cm² but higher levels can be used. During the current limited period the applied potential supplied from the power supply gradually increases as the thickness of the oxide film grows. The voltage is increased to a predetermined limit, which is selected according to the properties required for the surface material of the metal. When the voltage limit is reached, for example to 100 V, the current falls back to a low level, for example less than 1 mA/cm² and this drop in current level indicates that passivation has occurred. Once passivation occurs, the voltage is maintained to allow for surface engineering of the passivated metal surface, and during this step pits are formed in the surface. The voltage level and the time selected for applying the voltage can be chosen according to the coverage and dimensions of the pits required for the surface so this allows for precise surface engineering of the metal surface.

Once pores/pits are formed in the surface of the metal, surface engineering of the metal surface may also be employed to increase the loading of biocidal ions in the pits in the metal. Once the pits are formed, there may be surface engineering during step (b) where a subsequent change in voltage is applied to the metal or its alloy, for example to 20 V, 30 V or 75 V in the case of titanium, and this change in voltage can result in breakdown of the surface in areas where there are defects in the surface or where there are local areas of small pits. The change in voltage can cause existing pits/defects in the surface to grow by widening in diameter and deepening due to the fact that the walls of the pits remain electroactive.

During high voltage anodisation of an implant including titanium, hydrogen peroxide is produced through the oxidation of water at the interface with a semiconductor electrode according to the following equation:

$$2 H_2O \rightarrow H_2O_2 + 2H^+ + 2e^-$$

This can complex with $TiO^{2+}$ produced by corrosion at pits through the protective anodic film to form the highly soluble complex $TiO_2^{2+}$ (peroxy-titanyl), through the reaction:—

$$TiO^{2+} + H_2O_2 \rightarrow TiO_2^{2+} + H_2O$$

The titanium oxide complex remains within the pit in the surface of the metal (unless the surface is subjected to rinsing or stirring). Once the passivation and the production of pits to a required format is complete, the metal object is subjected to treatment with a chemical reductant to convert the peroxy-titanyl to $Ti(OH)_4$ (hydrous titania or HTiO).

Following anodisation, chemical reduction takes place. For this invention, several chemical reductants were tested to see if they were suitable for use in the chemical reduction stage. To do this small polished Ti6Al4V alloy test discs were mounted on a threaded contact and ultrasonically cleaned in acetone. Seven discs were used and the discs were rinsed in deionised (DI) water, ultrasonically cleaned in 1 M NaOH, rinsed again in DI water and then anodised in 2.1 M $H_3PO_4$ at 20° C. increasing the voltage to 15 V at 0.5 V/s, restarting and raising the voltage to 100 V at 0.5 V/s—holding at 100 V for 10 minutes, dropping the voltage to 20 V and holding for 20 minutes. Samples 3, 5-8 were disconnected, and samples 5-8 removed from the electrolyte for immersion in a range of reductant solutions; sample 3 was connected to a mild steel electrode immersed in the electrolyte for 4 minutes (equivalent to −0.66 V AgCl/Ag), while samples 1-2 underwent an electrochemically induced reduction step (by the application of a negative voltage of −0.45 V (AgCl/Ag) for 2 minutes. Samples 5-8 were immersed with the minimum of solution disturbance into 0.1 M reductant solutions of KBr, $(NH_4)_2Fe(SO_4)_2$, $NaNO_2$ and $Na_2SO_3$ for 7 minutes. All the samples were then removed and rinsed in DI water before immersion in stirred 0.1 M $AgNO_3$ for 1 hour silver loading. Silver assays were conducted by extracting the silver from the samples and analysing them using ICP-MS.

On reduction, hydrous titania is formed according to the equation:

$$TiO_2^{2+} + 2H_2O + 2e^- \rightarrow Ti(OH)_4$$

The reduction can be performed electrochemically by applying a reverse (negative) voltage to the implant, and the negative voltage, when using 2.1 M phosphoric acid as electrolyte, is preferably between −0.2 to −0.7 V with respect to an Ag/AgCl standard reference electrode. This voltage range is low enough to avoid electrolysis of the water solvent. Chemical reduction using a corrodible metal (such as iron) is analogous to an electrochemical reduction, and also imposes a negative voltage on the implant, but without using an external cell or source of electricity.

The silver solution is an aqueous solution of silver nitrate having a silver concentration in the range of from 0.001 to 10 M, e.g. 0.01 to 1.0 M, for example, 0.1 M or thereabouts. When the treated surface from an acid environment is subsequently placed in 0.1 M $AgNO_3$ solution (pH ~4), an ion-exchange reaction is then able to take place.

$$HTiO-H^+ + Ag^+ \rightarrow HTiO-Ag^+ + H^+$$

The treated implant may have a silver content of 0.1 to 100 μg/cm², 0.5 to 40 μg/cm² or more typically from 2-μg/cm². The silver is present initially mainly in ionic form but may be at least partially converted to atomic clusters of metal dispersed within the hydrous titania adsorption matrix as a result of photo-reduction. Typically, ~0.3-1 μg/cm² is adsorbed on the hard passive layer, with the remainder stored within the hydrous titania-filled pits.

The hydrous titania is an inorganic ion-exchange medium that can become saturated with cations such as silver cations when contacted with silver nitrate, $AgNO_3$, solution and this results in an increased level of silver. Hydrous titania is also known to be a catalyst for the photoreduction of silver cations to the metallic species, which may result in the conversion of some of the adsorbed ionic silver to dispersed metallic silver within the adsorber matrix.

If the reductant solution were alkaline, then the HTiO would have adsorbed hydroxyls on it. As a result, the $AgNO_3$ solution would need to be mildly acidic to avoid precipitation of $Ag_2O$ (pH<7).

$$HTiO-OH^- + H^+ + Ag^+ \rightarrow HTiO-Ag^+ + H_2O$$

The following Table 1 shows the summary of anodising and silver loading data. The values given per unit area are those calculated on the basis of the microscopic surface area (subscript m) and the geometric surface area (subscript g).

TABLE 1

| | Disc | | | | | | |
|---|---|---|---|---|---|---|---|
| | 1 EC reduction | 2 | 3 Fe contact | 5 KBr | 6 Fe(II) | 7 NaNO$_2$ | 8 Na$_2$SO$_3$ |
| Ag assay (μg/disc) | 10 | 13 | 17 | 16 | 8.7 | 21 | 7.9 |
| μg/cm$^2_{-m}$ | 2.42 | 2.91 | 3.89 | 3.81 | 1.89 | 4.16 | 2.03 |
| μg/cm$^2_{-g}$ | 3.38 | 4.41 | 5.72 | 5.34 | 2.93 | 7.05 | 2.68 |

This data is shown in FIG. 1 where it can be seen that under the experimental conditions described the highest silver loading is found with NaNO$_2$, followed closely by the Fe contact, KBr and then electrochemical reduction (EC), which is used for comparison. Neither Fe(II) nor Na$_2$SO$_3$ were as effective as NaNO$_2$. Where there is increased Ag loading the samples have darkened areas when viewed under an optical electron microscope.

It is also noted that using Fe reduction electrodes does not require the removal of the sample from the anodising electrolyte prior to reduction. This would minimize the loss of any peroxy-titanyl produced at the surface of the implant upon removal from the electrolyte and immersion in a separate reductant, which would result in a decrease in the inventory of HTiO produced at the surface, and hence a smaller Ag loading by subsequent ion-exchange. That is to say, this avoids washing the peroxy-titanyl off the surface by removing it from the electrolyte, although the electrolyte would become progressively contaminated with cations of iron produced by corrosion (or of zinc, if a zinc reduction electrode were used). This contamination could be prevented by separating electrolyte that is in contact with the corrodible metal from electrolyte in contact with the sample by a salt bridge, or by an ion-selective membrane such as an anion-selective membrane.

For metal substrates—especially those non-titanium based materials e.g. Nb, Ta, Zr and their alloys—using a chemical reducing agent may be a useful method of introducing a hydrous metal oxide adsorber medium into the surface, prior to subsequent biocide adsorption. The adsorber can be based on the metal from which the implant is made, for example, zirconium, but for cost effectiveness, titania is used as a preference.

The anodising process forms a hard surface that can have different coloured appearances due to optical interference effects. During the initial steps of anodising, the surface colour varies from gold to purple, blue, through to colourless, green, yellow, orange and finally red/purple. Anodising at 100 V produces a film thickness of about 140 nm. Changing the voltage can alter the extent of anodising and hence the thickness of the hard surface, which in turn influences the colour formed. Different voltages alter the colour produced, for example in 2.0 M phosphoric acid, approximately 20 V, up to 35 V will produce a blue colour on the metal, e.g. an implant or jewellery. Having different coloured articles, not only provides different aesthetic effects but also allows for articles such as implants to be identified, for example, an implant for one purpose or from one manufacturer can be colour coded so that if it has to be removed or replaced, a medical practitioner can identify that implant as being of a certain type and they can then replace it with another implant of the same type. In the case of jewellery, different colours provide different degrees of attractiveness and this is particularly applicable to titanium based jewellery.

It is thought that during exposure to body fluids, there is a slow leaching of silver species from the anodised layer, so that the growth of microorganisms such as bacteria, yeasts or fungi in the vicinity of the metal object is inhibited. The leaching is believed to be primarily effected by ion exchange of silver on the metal object with sodium in the body fluids that contact the metal object. Other mechanisms such as the oxidation of the metallic silver to ionic species by means of the localised oxygen levels can also occur to produce the released silver ions which can go on to kill or suppress the growth of the microorganisms or the biofilm formation.

The method of the invention described hereinabove may be employed for the preparation of a range of metal objects which involve the treatment with an anodising electrolyte. In particular, the invention has applications to metal articles that are formed of titanium or which are titanium alloys, and those of zirconium, niobium, tantalum or their alloys.

It is to be understood that references herein to silver as a biocidal metal also apply to other biocidal metals, such as copper, gold, platinum, palladium or mixtures thereof, either alone or in combination with other biocidal metal(s).

It is also envisaged that a bone promoting material may be coated on the metal implant once the biocidal material has been introduced, such as hydroxyapatite.

Although individual embodiments of the invention are discussed, it is to be understood that combinations of the individual embodiments fall within the scope of the invention as claimed and described.

What is claimed:

1. A method of treating a metal object so as to form thereon a surface layer which is integral with the metal object, and which includes a biocidal metal, the method comprising:
   (a) immersing the metal object, which is to provide a substrate for the surface layer, in an anodising electrolyte containing a solvent, and anodising the metal, by application of a positive voltage, to form an anodised integral surface layer on the metal object, wherein the metal of the metal object comprises titanium, niobium, tantalum, zirconium and/or an alloy thereof;
   (b) continuing the application of a positive voltage to produce pits through the integral surface layer and into the substrate;
   (c) producing a hydrous metal oxide in the pits by treating the metal object with a chemical reducing agent after steps (a) and (b), by connecting a corrodible metal in solid form to the metal object to act as a reductant, wherein the corrodible metal is in contact with the metal object through an electrical connection and the corrodible metal is in ionic connection with the metal object through an electrolyte, and wherein the corrodible metal corrodes preferentially to the metal object; and
   (d) contacting the anodised metal object resulting from step (c) with a solution containing a biocidal metal so as to incorporate said biocidal metal into the surface layer.

2. The method according to claim 1, wherein the corrodible metal is Fe or Zn or an alloy thereof 3. The method of claim 1 wherein the anodising is performed employing an electrolyte comprising phosphoric acid, sulphuric acid, acetic acid or an alkaline base.

4. The method of claim 3 that uses phosphoric acid at a concentration in a range of from 0.01 to 5 molar.

5. The method of claim 1 wherein the anodised metal object is treated with a solvent to remove electrolyte and soluble cations prior to contacting the anodised metal object with the solution containing a biocidal metal.

6. The method of claim 1 wherein the anodising is performed with a current density in the range from 0.1 to 25 mA/cm$^2$.

7. The method of claim 1 wherein during the anodising, movement of the electrolyte relative to the surface of the metal object is inhibited or suppressed, at least during the pit growth phase of step (b).

8. The method of claim 1 wherein the biocidal metal comprises copper, gold, platinum, silver or mixtures thereof.

9. The method of claim 8 wherein the biocidal metal comprises silver.

10. The method of claim 1 comprising multiple anodisation steps of anodising the metal by application of a positive voltage.

* * * * *